United States Patent [19]

Charnley

[11] 4,327,449

[45] May 4, 1982

[54] ACETABULAR PROSTHESIS

[75] Inventor: John Charnley, Knutsford, England

[73] Assignee: Charnley Surgical Inventions Limited, Knutsford, England

[21] Appl. No.: 163,311

[22] Filed: Jun. 26, 1980

[30] Foreign Application Priority Data

Jul. 10, 1979 [GB] United Kingdom ............... 23961/79

[51] Int. Cl.³ ............................................. A61F 1/03
[52] U.S. Cl. ..................................... 3/1.912; 128/92 C
[58] Field of Search ........................... 3/1.912, 1.913; 128/92 C, 92 CA

[56] References Cited

U.S. PATENT DOCUMENTS 2,947,308  8/1960  Gorman ............................ 3/1.912 X
4,173,797  11/1979  Langlais et al. ...................... 3/1.912

FOREIGN PATENT DOCUMENTS 2823306  12/1978  Fed. Rep. of Germany ....... 3/1.912
1047640  7/1953  France ............................. 128/92 C

*Primary Examiner*—Clifford D. Crowder
*Attorney, Agent, or Firm*—Ross, Ross & Flavin

[57] ABSTRACT

An acetabular prosthesis comprises a body 41 of plastics material defining a part-spherical socket cavity 43 surrounded by a rim 44. A flange extends outwardly from the rim 44. At 48 it inclines from the rim 44 in the direction of the body 41 and at 49 it inclines from the rim in a direction away from the body 41, while lobes 46, 47 therebetween are correspondingly curved. This arrangement provides for a considerably increased area of bone in the acetabulum to be available as a cementing surface when the prosthesis is fitted into a reamed out hip acetabulum in the special circumstances of the invention which is that the axis of socket cavity 43 extends substantially transversely with no or little anteversion.

9 Claims, 10 Drawing Figures

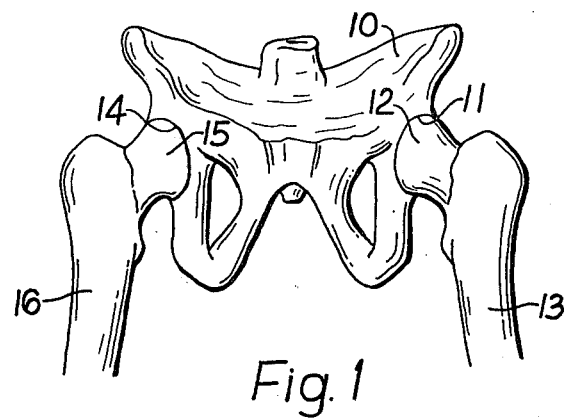
Fig. 1
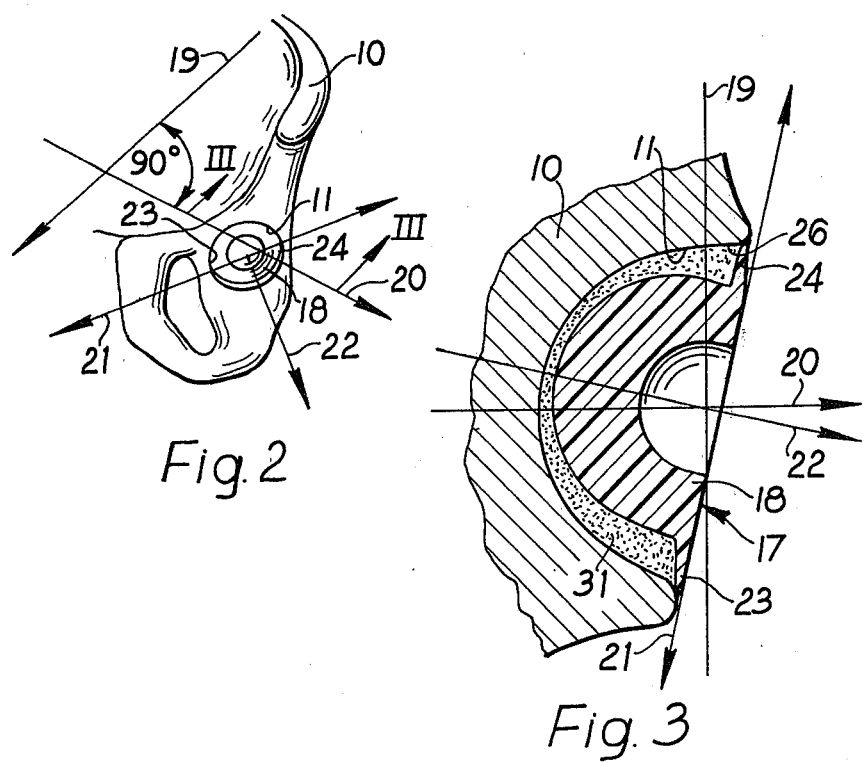
Fig. 2
Fig. 3

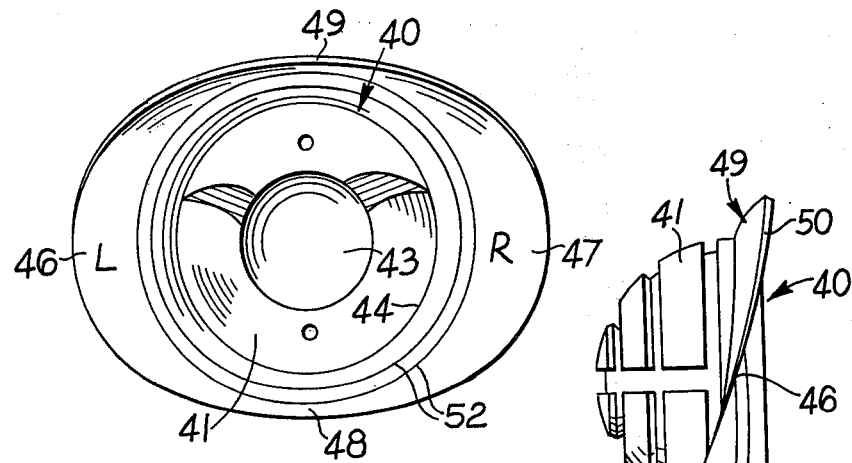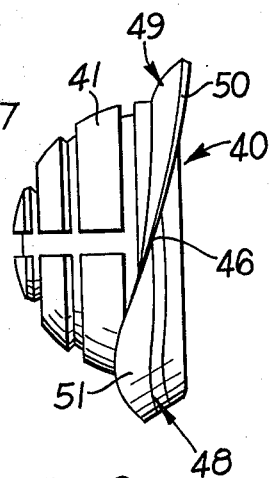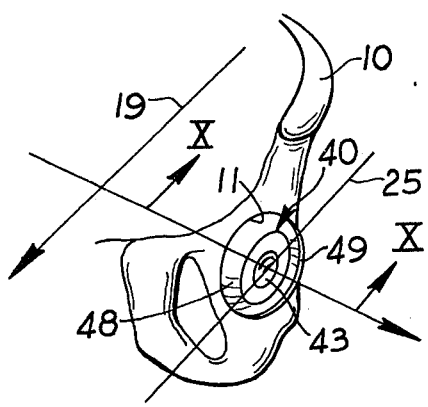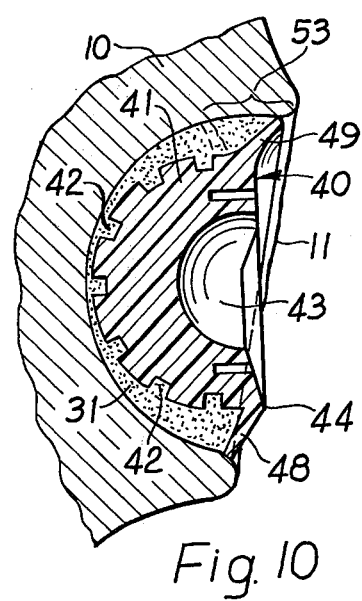

ACETABULAR PROSTHESIS

This invention concerns an acetabular prosthesis, that is to say the socket member of an artificial hip joint.

In the past, it has been customary to design acetabular prostheses as simple hemispheres provided with a rim symmetrical about the central axis of the socket. These simple forms have been placed in the anatomical acetabulum with their rims more or less in the same plane as the plane of the face of the anatomical hip joint socket. This plane, generally speaking, is such that the axis of the normal socket is directed laterally, downwards, and forwards. The downward component is at about 45° to the horizontal and the anterior component is approximately 20° to 30° anterior to the lateral plane.

FIG. 1 is a diagrammatic fragmentary front perspective view illustrating a human pelvis with the heads of corresponding thigh bones or femurs located in respective sockets or acetabular of the thigh bones thereof;

FIG. 2 is a diagrammatic fragmentary front perspective view illustrating, schematically, how an acetabular prosthesis, not of the invention, would normally be fitted into one of the hip bones of FIG. 1;

FIG. 3 is an enlarged horizontal section through the prosthesis of FIG. 2, the section corresponding to the line III—III in FIG. 2;

FIG. 7 is a front view of a preferred embodiment of the acetabular prosthesis of the invention;

FIG. 8 is an end view of the prosthesis of FIG. 7;

Figure 4:
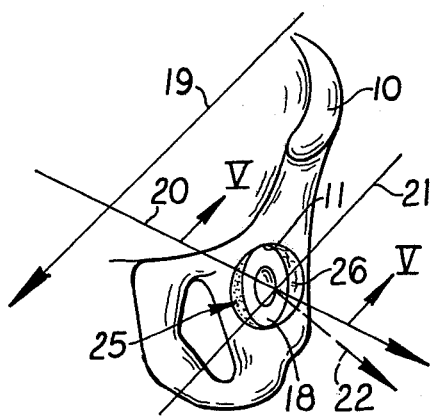
FIG. 4 is a view similar to FIG. 2 but showing the prosthesis differently fitted.

FIG. 9 is a diagrammatic fragmentary perspective view similar to FIGS. 2 and 4, but showing the acetabular prosthesis of FIGS. 7 and 8 fitted in place; and FIG. 10 is a view similar to that of FIG. 4 but showing the preferred prosthesis, of FIGS. 7 and 8 in the acetabulum, the horizontal section being taken as indicated at X—X in FIG. 9.

In FIG. 1, a human pelvis indicated generally by the reference numeral 10 comprises a left hip bone having a left acetabulum 11 accommodating head 12 of left thigh bone or femur 13 and a right acetabulum 14 accommodating head 15 of right thigh bone or femur 16.

FIGS. 2 and 3 diagrammatically illustrate how, in ordinary practice, an acetabular prosthesis or artificial socket member 18 would usually be fitted into the acetabulum 11 by means of a grouting of a non-adhesive (plastics) cement 31 so as to conform to the anteversion of the normal acetabulum 11. In FIG. 2, the arrows 19, 20 indicate respectively the anatomically forward and lateral directions of the hip bone relative to the vertical, standing position of the patient. The arrow 21 serves to indicate that the plane of the face of the prosthesis 18 is anteverted to correspond to the anteversion of the plane of the face of the natural acetabulum 11. Arrow 22 corresponds to the direction of the axis of the prosthesis 18, from which it will be seen that the tilt thereof also has a downward component.

FIG. 3 is a horizontal cross section corresponding to what is shown in FIG. 2 and indicates how the tilt of rim 17 of the simple design of socket member 18 corresponds with the orientation of the normal acetabulum 11 being nearer to the midline of the patient at the front and more laterally disposed at the back.

The essential result of the presence of the anterior component 21 in the simple design of socket is that the anterior lip 23 of the rim 17 of the prosthesis 18 is at a higher level than the posterior lip 24 of the rim when the whole orientation is seen at a higher horizontal level than the section in FIG. 3 which is through the centre of the socket. This orientation imitates the inclination of the anatomical acetabulum 11 and this is regarded by many surgeons as helpful in promoting a free range of flexion of the hip. Some surgeons believe that, if the anterior lip 23 of the socket member or prosthesis 18 is at the same level as the posterior lip 24, impingement of the neck of the femoral prosthesis (not shown) which fits into the socket member 18, will take place and prevent flexion beyond 90° from the extended position.

The disadvantage of giving the anatomical tilt to an artificial acetabulum is that the more the socket member has an anterior component in the tilt the more the anterior and superior aspects of the metal sphere of the femoral prosthesis become exposed in the extended position of the hip which is the load-bearing position. This has two disadvantages: namely (1) that it reduces the area of the socket cavity transmitting load to the femoral prosthesis, hence encouraging wear; and (2) it lays the artificial joint open to the possibility of the head subluxating from the socket in a forward direction when the thigh is in full extension and experiencing an external rotation force.

Practical experience has shown that flexion of an artificial joint is not obstructed by implantation of the socket member 18 without an anterior component in the direction of the axis because a patient can externally rotate the femur in the extreme position of flex (as when tying a shoe lace) and so accommodate to impingement of the neck of the femur against the internal rim of the socket member 18. It is thus possible to have maximum cover for the superior surface of the sphere of the femoral component in the standing and walking position without an important loss in the range of flexion.

Figure 5:
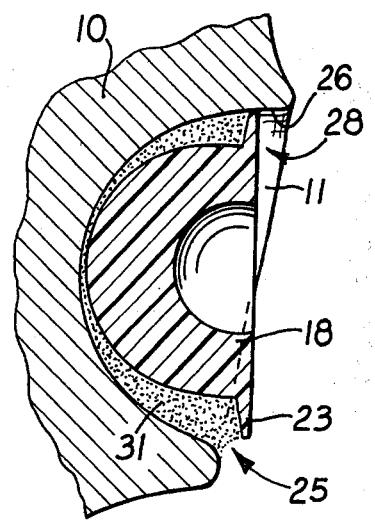
FIG. 5 is a horizontal section corresponding to the line V—V of FIG. 4.

In the conventional designs of socket member 18 which have a simple rim which is symmetrical round the axis of the socket it is impossible to orientate the member 18 in the natural acetabulum 11 so as to avoid an anterior component without failing to use the full surface area of bone on the posterior lining of the acetabulum for contact with the cement 31 used to bond the socket 18 with the acetabulum 11. This will be understood from FIGS. 2 and 3 which show how an element of anteversion permits the anterior lip 23 and the posterior lip 24 of the rim 17 of the socket member 18 to approximate to the anatomical rim of the acetabulum 11. FIGS. 4 and 5 show how, in position without anteversion, a conventional design of socket member 18 will expose cement at the anterior part 25, and the posterior bony rim part 26 of the acetabulum will be left uncovered by the socket member 18 and an area of bone, indicated at 28 in FIG. 5, in the acetabulum 11 available for contact with cement will fail to be employed for bonding purposes.

Figure 6:
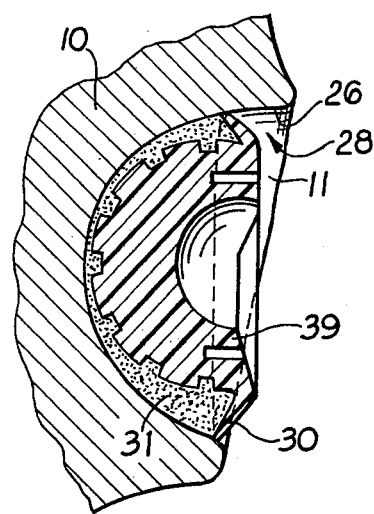
FIG. 6 is a view similar to FIG. 5 but showing a previous practical proposal.

FIG. 6 shows how the exposed cement 25 in correspondence with the anterior lip 23 of the socket member has, in the past, been overcome by the inventor of the present invention by providing a socket member 39 with a peripheral flange 30 extending in the direction of the body of the socket member and inwardly, that is to say away from the face of the member, i.e. towards the midline of the patient's body.

It will readily be perceived from FIG. 6 that the flange 30 provides the advantage that it eliminates the exposed cement 25 of FIG. 5, providing a component masking such cement region 25 and ensuring that the latter contributes to the security of the socket member 39 within the acetabulum 11.

However, whilst the inwardly-directed flange 30 provides this advantage at the anterior position, it will readily be appreciated, from consideration of FIG. 6, that it is accompanied by what is almost an equivalent disadvantage at the posterior position, in that it increases the area 28 of the exposed posterior rim part 26 as compared with the area which would be exposed as in FIG. 5 or if the flange 30 were generally coplanar with the rim of the socket member 18 as in FIG. 3. Accordingly, it does not permit full use to be made of the entire interior wall area of the reamed-out acetabulum 11 for cementing purposes.

An object of the present invention is to provide an improved acetabular prosthesis whereby this disadvantage is eliminated, better use of the posterior internal surface of the acetabulum being possible, to contribute to the strength of the fixing of the prosthesis in the actabulum.

With this object in view, the present invention provides an acetabular prosthesis comprising a body of plastics material defining a blind, part-spherical socket surrounded by a rim, and a flange around said body and extending outwardly from the rim, said flange inclining in the direction of or towards the body of the socket member over approximately half of the periphery of the rim, the rest of the flange inclining in a direction away from the body or being substantially coplanar with the rim.

Over the remaining half of the periphery of the rim the flange extends in a direction away from the body of the socket member.

The flange preferably comprises two crescent-shaped diametrically-opposite lobes inter-connected by narrower transitional portions, one transitional portion being substantially at the middle of the rear-wardly-extending portion and the other being in the plane of the rim or forwardly inclined. In use, one or the other of the lobes can be removed and the remainder of the flange trimmed as required, enabling the two-lobe prosthesis to be used in either a left acetabulum or a right acetabulum.

The preferred prosthesis 40 of the invention is made from high-density polyethylene and has a generally hemispherical body 41 having outer grooves 42 for forming a key with the acrylic cement 31 used to adhere it into the acetabulum 11. The body 41 has a central blind part-spherical socket cavity 43 for engagement therein of the head of a femoral prosthesis (not shown). The socket cavity 43 is surrounded by a rim 44. A flange 45 extends outwardly of the rim 44 and in the manufactured condition (FIGS. 7 and 8) comprises two generally crescent-shaped diametrically-opposite lobes 46, 47 connected by relatively narrower portions 48 and 49. The connecting portion 48 inclines from the rim 44 in the direction of the body 41 at an angle of between 35° and 55° (preferably 45°) and the connecting portion 49 inclines from the rim 44 in a direction away from the body 41, also at an angle of between 35° and 55° (preferably 45°). From FIG. 8 it will be apparent that each lobe 46, 47 has a respective forwardly-extending part 50 and a rearwardly-extending part 51.

When the prosthesis 40 is to be used, one of the lobes 46 and 47 is substantially removed by cutting down to or to adjacent one or other of cutting guide lines 52. The connecting portions 48 and 49 are trimmed also so that the flange part remote from the remaining lobe has its periphery generally part-circular. The actual place of cutting will be dependent upon the size of the reamed-out acetabulum 11, and the decision will be made during arthroplasty. If, as shown in FIGS. 9 and 10, a left acetabulum 11 is involved, the lobe 46 marked "L" will remain and if a right acetabulum is involved the lobe 47 marked "R" will remain.

Upon installation in the reamed-out acetabulum 11, the prosthesis 40 takes up the position shown in detail in FIG. 10, and it will be seen that the area of the cement joint (which is bounded by the peripheral edge of the flange) is substantially increased and substantially the entire inner wall surface of the acetabulum 11 is used. The area of the increase is widest at the middle of the posterior wall (as indicated by numeral 53) and tapers to zero at a diametrically opposite location. This increased cementing area ensures that the strength of the fixing of the prosthesis is a significantly increased (for example by as much as 20%) as compared with the arrangement of FIG. 6.

The invention is not limited to the precise details of the foregoing example of FIGS. 7 to 10, and variations may be made thereto. In particular, the connecting portion 48 of the flange remote from the connecting portion 49 does not have to extend in a direction away from the body 41 but may be substantially co-planar with the rim 44. Significant increase of the join area is still achieved.

I claim:

1. An acetabular prosthesis comprising: a body of plastics material defining a blind part-spherical socket surrounded by a rim, and a flange around the body and extending outwardly from the rim, the flange inclining toward the body of the socket over approximately half of the periphery of the rim, the rest of the flange inclining in a direction away from the body of the socket.

2. A prosthesis as claimed in claim 1, wherein the flange is of varying width, having two diametrically-opposed lobes.

3. A prosthesis as claimed in claim 2, wherein the lobes are substantially crescent shaped.

4. A prosthesis as claimed in claim 2, wherein one part of the connecting portion of the flange between the lobes extends towards the body and the other part of the connecting portion extends in a direction away from the body.

5. A prosthesis as claimed in claim 2, wherein the flange is marked with cutting lines for facilitating removal of one lobe before use.

6. An acetabular prosthesis comprising: a body of plastics material defining a blind part-spherical socket surrounded by a rim, and a flange around the body and extending outwardly from the rim, the flange inclining toward the body of the socket over approximately half of the periphery of the rim, the rest of the flange being substantially co-planar with the rim.

7. A prosthesis as claimed in claim 6, wherein the flange is of varying width, having two diametrically-opposed lobes.

8. A prosthesis as claimed in claim 7 wherein said lobes are substantially crescent shaped.

9. A prosthesis as claimed in claim 7, wherein the flange is marked with cutting lines for facilitating removal of one lobe before use.

* * * * *